United States Patent [19]

Ohe et al.

[11] Patent Number: 4,837,170

[45] Date of Patent: Jun. 6, 1989

[54] MONOCLONAL ANTIBODY, MEASURING METHOD OF GLUCOSYLATED PROTEIN BY UTILIZING THE MONOCLONAL ANTIBODY, AND KIT THEREFOR

[75] Inventors: Yasuo Ohe; Makiko Matsuura, both of Tokushima; Fumio Shimizu, Naruto; Yoshito Nakajima, Tokushima; Shin Sadahito, Tokushima; Kenji Shima, Tokushima, all of Japan

[73] Assignee: Otsuka Pharmaceutical Co., Ltd., Tokyo, Japan

[21] Appl. No.: 3,144

[22] Filed: Jan. 14, 1987

[30] Foreign Application Priority Data

Jan. 20, 1986 [JP] Japan .................................. 61-10758
Mar. 17, 1986 [JP] Japan .................................. 61-58828

[51] Int. Cl.$^4$ .................... G01N 33/577; G01N 33/66
[52] U.S. Cl. ................................ 436/548; 435/172.2; 435/240.27; 436/67; 436/808; 436/811; 530/387; 935/110
[58] Field of Search .................. 436/808, 67, 548, 513, 436/811; 435/172.2, 240.27; 935/110; 530/387

[56] References Cited

U.S. PATENT DOCUMENTS

| | | | |
|---|---|---|---|
| 4,247,533 | 1/1981 | Cerami | 436/808 X |
| 4,438,204 | 3/1984 | Deeg | 436/67 |
| 4,474,892 | 10/1984 | Murdd | 436/548 X |
| 4,618,486 | 10/1986 | Lundblad | 436/513 X |
| 4,629,692 | 12/1986 | Dean | 436/811 X |

OTHER PUBLICATIONS

S. Taneda et al., J. Japan Diab. Soc., 28(5), 695–698 (1985).
G. Koehler et al, "Continuous Cultures of Fused Cells Secreting Antibody of Predefined Specificity", Nature, 256, 495–497, (1975).
Witztum et al., "Nonenzymatic Glycosylation of Homologous Low Density Lipoprotein and Albumin . . . " Proc. Natl. Acad. Sci., USA 80, 2757–2761 (1983).
Witztum et al.; "Autoantibodies to Glucosylated Proteins in the Plasma of Patients with Diabetes Mellitus"; Proc. Natl. Acad., Sci. USA, 81 3204–3208 (1984.)
Witztum et al., "Nonenzymatic Glucosylation of Low--Density Lipoprotein Alters Its Biologic Activity", Diabetes, 31, 283–291 (1982).
Steinbrecher et al.; "Glucosylation of Low–Density Lipoproteins to an Extent Comparable to That Seen in Diabetes Slows . . . " Diabetes, 33, 130–134 (1984).
Gafre et al.; "Preparation of Monoclonal Antibodies: Strategies and Procedures"; Methods in Enzymology, 73, 3–46 (1981).
Curtis et al.; "A Novel Method for Generating Region-Specific . . . " J. Clin. Invest., 72, 1427–1438 (1983).

*Primary Examiner*—Sidney Marantz
*Attorney, Agent, or Firm*—Oblon, Fisher, Spivak, McClelland & Maier

[57] ABSTRACT

For the diagnosis of diabetes, a glucosylated protein in a sample is measured by subjecting the sample to a reducing treatment and then detecting a compound, which contains one or more reduced glucosylated lysine residual groups, in accordance with an immunoassay technique in which the reduced glucosylated lysine residual groups are used as an epitope.

9 Claims, 6 Drawing Sheets

MONOCLONAL ANTIBODY, MEASURING METHOD OF GLUCOSYLATED PROTEIN BY UTILIZING THE MONOCLONAL ANTIBODY, AND KIT THEREFOR

BACKGROUND OF THE INVENTION

1. Field of the Invention

This invention relates to a monoclonal antibody, a method for the measurement of a glucosylated protein by using the monoclonal antibody, said method being useful for the diagnosis of diabetes, and a kit for the measurement, as well as a glucitol-lysine derivative useful in the practice of the measuring method.

2. Description of the Prior Art

In recent years, non-enzymatic sugar-protein binding reactions are found to take place in organisms, especially, in those of diabetics. Such non-enzymatic binding reactions are those between aldehyde groups of glucose contained at a high concentration in blood and N-terminal and side-chain amino groups of proteins having relatively long half-life periods and contained in organisms. It has also been elucidated that aldimine (Schiff's base) bonds, which are formed by the above binding reactions, are converted into stable keto-amine bonds through the Amadori rearrangement, thereby forming glucosylated proteins. It has also been revealed that the measurement data of these glucosylated proteins are closely correlated with blood sugar levels during fasting and moreover, the data of diabetic subjects are high enough to distinguish them clearly from the corresponding data of non-diabetics. Accordingly, such glucosylated proteins are effective as indices for controlling blood sugar levels. Their measurement data are useful for the diagnosis of diabetes, the assessment of pathemas, prognostication, and the like. The measurement of glucosylated proteins has therefore great clinical significance.

As methods for the measurement of the above-mentioned glucosylated proteins, there has conventionally been known the TBA (Thiobarbituric acid) method, namely, to add a mild acid to serum and then to heat the resultant mixture to release 5-hydroxymethylfurfural (5-HMF), followed by colorimetric measurement of a color produced through the binding of 5-HMF with thiobarbituric acid (TBA); or the method using boric acid affinity chromatography, namely, to subject aminophenylboric acid to a gel column which has been prepared by immobilizing aminophenylboric acid on a suitable carrier such as "Sepharose CL-6B" (trade name) or the like to adsorb glucosylated protein by making use of protein-bound cis-diol groups of sugar, to elute and separate glucosylated proteins adsorbed on the gel, and then to subject the thus-separated glucosylated proteins to colorimetry by ultraviolet absorption or the Lawry's method.

With a view toward facilitating the operation and enabling fast measurements, it has also been studied to measure the above-mentioned glucosylated proteins by immunoassay. Some antiserum have already been proposed for such applications.

However, the conventional measuring techniques were still unable to meet the needs of the present field of art, especially, in view of accuracy and reproducibility in addition to operational problems such that the operation was complicated and long time was required for measurements [see, "Rinsho Kensa" MOOK, No. 18, pp 60-68 (1984) and Japanese Patent Laid-Open No. 119264/1984].

Under the above-described circumstances, there has been a strong demand in the present field of art for the development of a new measuring technique which can replace conventional methods for the measurement of glucosylated proteins, has still higher specificity enabling appropriate detection of non-enzymatic glucosylation in people to be tested, is hence excellent in accuracy and reproducibility, permits simple and fast measurements, and is also suitable as a screening method.

SUMMARY OF THE INVENTION

The present inventors have carried out an investigation with a view toward providing a novel monoclonal antibody for glucosylated proteins and hence, a novel immunoassay technique the development of which has been strongly desired in the present field of art.

In the course of the above investigation, it was presumed that $\epsilon$-amino groups of lysine residual groups in a protein would be glucosylated to form aldimine and a ketone by a non-enzymatic binding reaction between the protein and D-glucose, the degree of the non-enzymatic glucosylation could be determined by measuring a ketoamine, a rearrangement reaction product of aldimine, and the above determination could be practised by using an antibody capable of binding selectively to the ketoamine (in other words, capable of recognizing the ketoamine).

The above outlined approach was however unable to achieve the desired effects for the following reasons. At equilibrium, the above ketoamine exists in different steric configurations in a solution, namely, in the forms of a closed-ring ketose as well as the $\alpha$-and $\beta$-anomers of D-pyranose and D-furanose having 6-membered and 5-membered ring structures respectively. Even if a monoclonal antibody capable of selectively recognizing the ketoamine was employed in order to achieve the immunoassay measurement with a high sensitivity and accuracy, the monoclonal antibody recognized only one of the isomers due to its extremely high specificity in terms of recognition so that it was unable to detect the whole ketoamine.

The present inventors therefore proceeded further with the investigation. As a result, it has been found that the reduction of the above-described ketoamine provides a reduced glucosylated lysine adduct (glucitol-protein) stable in steric configuration too and the use of a sample, which has been subjected to a reducing treatment, as a test sample and a monoclonal antibody for the glucitol-protein provides a measuring technique making full use of advantages of the monoclonal antibody, leading to completion of this invention.

Accordingly, an object of this invention is to provide a monoclonal antibody capable of specifically recognizing reduced glucosylated lysine residual groups.

Another object of this invention is to provide a method for the measurement of a glucosylated protein by using the above monoclonal antibody and a measuring kit therefor.

A further object of this invention is to provide a glucitol-lysine derivative useful in the above-described measuring method.

In one aspect of the invention, there is thus provided a monoclonal antibody for reduced- glucosylated lysine residual groups as an epitope.

In another aspect of the invention, there is also provided a method for the measurement of a glucosylated protein in a sample, which comprises subjecting the sample to a reducing treatment and then detecting a compound, which contains one or more reduced glucosylated lysine residual groups, in accordance with an immunoassay technique in which the reduced glucosylated lysine residual groups are used as an epitope.

In a further aspect of the invention, there is also provided a diagnostic kit for diabetes, comprising a monoclonal for reduced glucosylated lysine residual groups as an epitope.

In a still further aspect of the invention, there is also provided a glusitol-lysine derivative represented by the following formula (I):

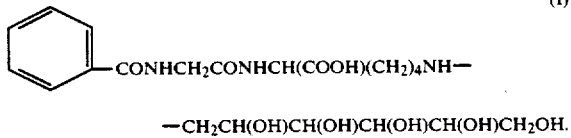

The monoclonal antibody of this invention can recognize reduced glucosylated lysine residual groups specifically. By using this antibody, it is therefore possible to precisely determine the degree of non-enzymatic glucosylation and hence to conduct effectively the diagnosis of diabetes in subjects and the control of their blood sugar.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
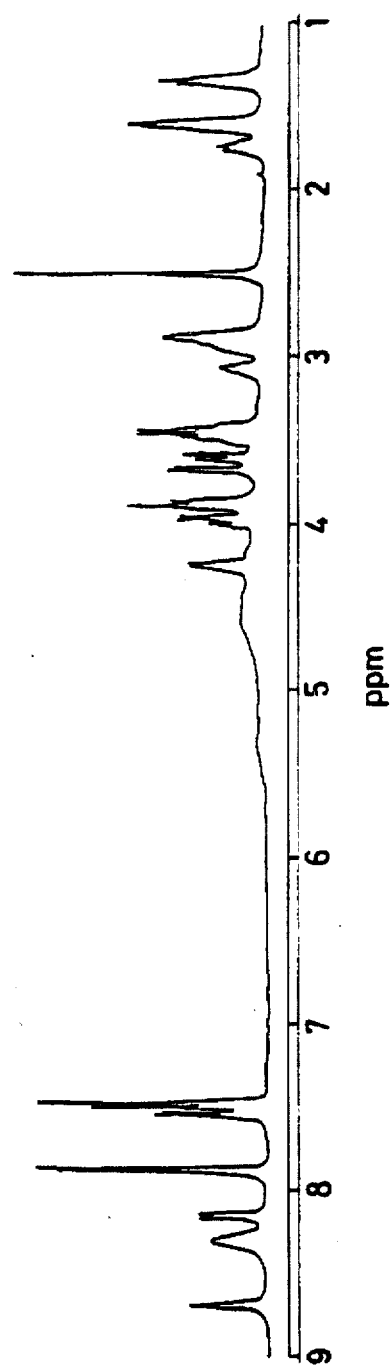
FIG. 1 is a PMR spectrum of a glucitol-lysine derivative (I) according to this invention.

The monoclonal antibody of this invention can be produced by a process known per se in the art, using as an immunogen an antigen which contains one or more reduced glucosylated lysine residual groups. More specifically, the following method may be mentioned by way of example. Plasma cells (immunocytes) of a mammal which has been immunized with the above-mentioned antigen are fused with plasmacytoma cells of a mammal to form hybridomas. A clone capable of producing an antibody, which can recognize reduced glucosylated lysine residual groups, is selected from the hybridomas. The intended antibody (monoclonal antibody) is then obtained from the clone.

In the above-described method, a reduced glucosylated lysine (glucitol-lysine) or reduced glucosylated protein (glucitol-protein) in which one or more reduced glucosylated residual groups are bound to lysine or via lysine residual group or groups to a carrier protein may generally be used as a starting antigen. Namely, various protein derivatives can be used so long as they have the reduced glucosylated lysine structure. As their representative examples, may be mentioned reduced glucosylated β-lipoprotein (Glc-LDL), reduced glucosylated polylysine (Glc-PL), reduced glucosylated human serum albumin (Glc-HSA), reduced glucosylated bovine serum albumin (Glc-BSA), glucitol-lysine (Glc-L), etc. In addition, it is also possible to use a glucitol-lysine derivative synthesized for the first time by Ohe et al. and represented by the following formula (I):

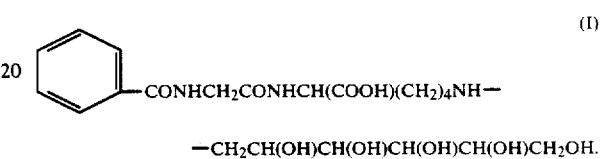

The production of these antigens can be carried out in a manner known per se in the art. They may each be produced, for example, by subjecting a bound substance (aldimine or ketoamine), which has been obtained through a non-enzymatic binding reaction of lysine or a carrier protein and D-glucose, to a reducing treatment. The above non-enzymatic binding reaction can be carried out by a usual method, for example, by incubating the reactants at about 20°–37° C. for about 72–180 hours in a suitable medium such as a conventional buffer. On the other hand, the reducing treatment can generally be effected in accordance with a reaction method which is routinely employed in the reduction of Schiff's bases or in the reduction of a carbonyl group into a hydroxyl group. As its specific example, may be mentioned a reducing method which employs a hydride-type reducing agent such as $NaBH_4$ or $NaCNBH_3$ In general, these reducing agents may each be used approximately in an equimolar to twofold molar amount based on D-glucose employed in the treatment. The treatment may be applied at about 20°–37° C. for about 72–180 hours.

No particular limitation is imposed on the mammal to be immunized with the antigen in the above-described method. It is however preferable to choose a suitable mammal in view of its compatibility with plasmacytoma cells to be used for the cell fusion. In general, a mouse, rat or the like can be advantageously used.

The immunization is effected by a method known per se in the art, for example, by administering the above-described antigen to a mammal in accordance with intravenous, subcutaneous or intraperitoneal injection or the like. More specifically, it is preferable to dilute the antigen to a suitable concentration with PBS or the like and then to administer the thus-diluted antigen several times with an interval of 2–14 days to a mouse until the total dose reaches about 1–100 μg/mouse. As immunocytes, it is preferable to use spleen cells taken out about three days after the final administration.

As plasmacytoma cells of the mammal as the other parent cells to be fused with the above-described immunocytes, it is possible to use various cell strains already known in the art, for example myeloma cells such as p3 (p3/x63-Ag8) [Nature, 256, 495–497 (1975)], p3-U1 [Current Topics in Microbiology and Immunology, 81, 1-7 (1978)], NS-1 [Eur. J. Immunol., 6, 511–519 (1976)], MPC-11 [Cell, 8, 405–415 (1976)], SP2/0 [Nature, 276, 269–270 (1978)], FO [J. Immunol. Meth., 35, 1–21 (1980)], x63.6.5.3. [J. Immunol., 123, 1548–1550 (1979)], S194 [J. Exp. Med., 148, 313–323 (1978)], and R210 of rats [Nature, 277, 131–133 (1979)].

The fusion reaction of the above immunocytes and plasmacytoma cells can be conducted basically in accordance with a known method, for example, the method proposed by Milstein et al. [Method in Enzymology, Vol. 73, pp3 (1981)]. More specifically, the above fusion reaction can be effected, for example, in a usual nutrient medium in the presence of a fusion promoter. As the fusion promoter, it is possible to use one that is used routinely, for example, polyethylene glycol (PEG), Sendai virus (HVJ) or the like. It is also possible to add an auxiliary agent such as dimethyl sulfoxide in order to improve the efficiency of the fusion if desired. The immunocytes and plasmacytoma cells may be used at a ratio not different from their ratios in usual methods. For example, the immunocytes may be used in an amount of about 1–10 times the plasmacytoma cells. As the culture medium employed for the above-described fusion, it is possible to use, for example, the RPMI-1640 medium or MEM medium which is used for the multiplication of a cell strain of the above plasmacytoma cells, or any one of various routine media employed for culture of cells of the above sort. It is generally preferable to omit serum such as fetal calf serum (FCS). The above fusion is effected by mixing prescribed amounts of the above-described immunocytes and plasmacytoma cells thoroughly in the above-described medium, adding a PEG solution, which has been prepared for example by mixing PEG having an average molecular weight of 1000–6000 or so with a usual medium to a concentration of about 30–60 W/V% and has then been heated to about 37° C., and then mixing the resultant mixture. Desired hybridomas are then formed by repeating an operation in which a suitable medium is added, followed by centrifugation and removal of the resulting supernatant.

Isolation of the thus-obtained desired hybridoma is effected by culturing the resultant culture mixture in a conventional selective medium, for example, in the HAT medium (a culture medium containing hypoxanthine, aminopterin and thymidine). It is necessary to continue its culture in the HAT medium for a time period sufficient to kill all cells (unfused cells and the like) other than the intended hybridoma, usually, for several days to several weeks. The thus-obtained hybridomas are then cloned by usual limiting dilution and subjected to screening to detect a strain secreting the intended antibody.

The screening of the antibody-secreting strain may be effected by various methods employed routinely in the detection of antibodies [see, "Hybridoma and Monoclonal Antibodies" published by R & D Planning Co., Ltd. pp 30–53 (March 5, 1982)], including for example the ELISA method [Engvall, E., Meth. E. Enzymol., 70, 419–439 (1980)], plaque method, spot method, agglutination reaction method, Ouchterlony method, radioimmunoassay (RIA) method, etc. The detection can be carried out by using the above-described antigen. It is especially desirable to use an antigen different from that employed as an immunogen to eliminate any antibody which may potentially bind with antigen determinants other than reduced glucosylated lysine residual groups.

In the manner described above, it is possible to obtain desired hybridomas capable of producing an antibody which can recognize reduced glucosylated lysine residual groups. The hybridomas can be subcultured in a usual medium. It can also be stored with ease for a long period of time in liquid nitrogen.

The collection of the monoclonal antibody of this invention from the above hybridomas may be effected, for example, by culturing the hybridomas in a usual manner and then collecting the monoclonal antibody as the supernatant of the culture broth or by applying the hybridomas to a mammal compatible with the hybridomas, allowing the hybridomas to multiply and then obtaining the monoclonal antibody of this invention as an ascites fluid. The former method is suited for obtaining the antibody in a highly pure form, whereas the latter method is suited for the mass production of the antibody. The antibody, which has been obtained in the above-described manner, may then be purified by a usual purification method such as salting-out, absorption, gel filtration or affinity chromatography.

The thus-obtained monoclonal antibody of this invention has extremely high specificity to reduced glucosylated lysine residual groups. Accordingly, use of the antibody of this invention permits precise determination of the degree of non-enzymatic glucosylation in a subject. The thus-determined degree of non-enzymatic glucosylation in turn allows to achieve more accurate diagnosis of diabetes and control of blood sugar.

The method of this invention for the measurement of a glucosylated protein requires, as essential features thereof, the use of the monoclonal antibody of this invention and the employment of a reduction-treated sample as a test sample. Its basic operation may be practised by a usual immunoassay technique, for example, RIA, enzyme immunoassay (EIA), or the like. The operation, procedures and the like in these immunoassay techniques are not significantly different from those employed routinely. For example, the measuring method of this invention may be practised in accordance with the known competitive-binding method or sandwich method. The above-described antigen can be employed as an antigen for the measuring system.

As samples to be tested by the method of this invention, reduction-treated samples, for example, body fluids can be used. Illustrative examples of such body fluids may include blood, urine, intracellular fluid, lymph, pleural fluid, ascites fluid, amniotic fluid, gastric juice, pancreatic juice, cerebrospinal fluid, salivary juice and so on. The reduction treatments of samples such as these body fluids may each be effected in accordance with the above-mentioned method for producing the antigen, usually, by using a reducing agent at a concentration of about 10–100 mM and conducting the treatment for about 30 minutes–180 hours. It is most preferable to use these test samples after collecting their protein fractions (or removing glucose) prior to their reduction treatments. Such a pretreatment is also in conformity with the objects of this invention. The collection of the above-described fractions can be carried out by a method known per se in the art, for example, by a treatment method in which an organic solvent such as acetone, methanol, ethanol, propanol or dimethylformamide (DMF) is used as a protein precipitant, a treatment method in which a salting-out agent such as ammonium sulfate, sodium sulfate or sodium phosphate is used, an ultrafiltrating treatment method in which a dialysis membrane, flat membrane or hollow fiber membrane is used, or a combination of two or more of these methods. When a sample is purified up to an albumin or lipoprotein fraction in accordance with a known method and is then subjected to a reduction treatment for use as a test sample, it is possible to determine the degree of non-enzymatic glucosylation specific to a particular protein instead of the total amount of non-enzymatically glucosylated proteins.

In the method of this invention, the collection of a protein fraction prior to the above-described reduction treatment is effected more preferably by an adsorption treatment in which a suitable protein-adsorptive carrier is used. As the protein-adsorptive carrier, it is possible to use, for example, a carrier which has been obtained by immobilizing an antibody against a desired protein, such as anti-human serum albumin antibody, a particular pigment and the like on a usual insoluble carrier. As the pigment, may be mentioned "Coomassie Brilliant Blue (CBB)" (trade name), chlorotriazine dye or the like by way of example. "CBB-G250" (trade name) and "Cibacron Blue" (trade name) are more preferable. When a insolubilization method, in which a solidified reagent such as insolubilized antigen, insolubilized antibody or the above-mentioned protein-adsorptive carrier is used, is followed, the solidified reagent can be prepared by reacting the antigen, antibody or pigment chemically or physically with an insoluble carrier in a manner known per se in the art. As the insoluble carrier, it is possible to use, for example, cellulose, Sephadex (trade mark), Sepharose (trade mark), polystyrene, methyl methacrylate, acrylonitrile-butadienestyrene copolymer (ABS), styrene-maleic anhydride copolymer, filter paper, carboxymethylcellulose, ion-exchange resin, dextran, plastic film, plastic tube, nylon, glass beads, silk, polyamine-methyl vinyl ethermaleic acid copolymer, amino acid copolymer, ethylenemaleic acid copolymer or the like. The insolubilization (solidification) is effected by a chemical reaction such as diazo method as a covalent binding method, peptide method (acid amide derivative method, carboxychloride resin method, carbodiimide resin method, maleic anhydride derivative method, isocyanate derivative method, cyanogen bromide activated polysaccharide method, cellulose carbonate derivative method, a method making use of a condensing reagent, or the like), alkylating method, carrier binding method making use of a crosslinking reagent (glutar aldehyde, hexamethylene isocyanate or the like is used as the crosslinking reagent), or carrier binding method relying upon the Ugi reaction; an ion binding method employing a carrier such as an ion-exchange resin; a physical adsorption method using porous glass such as glass beads as a carrier; or the like.

As the labelled antigen or antibody, the above-described antigen or the antibody of this invention is used after labelling it with one of various usual labelling agents such as radioactive substances, enzymatic labelling agents and fluorescent substances. As a radioactive substance as the labelling agent, radioactive iodine isotopes such as $^{125}I$ may be mentioned. Exemplary fluorescent substances may include fluorescein isothiocyanate (FITC), tetramethyl rhodamine isothiocyanate (TRITC), substituted rhodamine isothiocyanates (XRITC), rhodamine B isothiocyanate, dichlorotriazine fluorescein (DTAF), etc. As illustrative examples of the enzymatic labelling agent, may be mentioned peroxidase (POX), microperoxidase, chymotrypsinogen, procarboxypeptidase, glyceraldehyde-3-phosphoric acid dehydrogenase, amylase, phosphorylase, D-nase, R-nase and the like. Labelling methods making use of these labelling agents can each be effected in a usual manner [see, J. Biol. Chem., 254, 9349–9351 (1979); Nature, 194, 495 (1962); Keiko Kotai Ho (Fluorescent Antibody Technique), Ikagaku Jikken Koza (Medicochemical Experiment Series), No. 4, 263–270; Acta. Endocrinol. Suppl., 168, 206 (1972); Proc. Nat. Acad. Sci., USA, 57, 713 (1967)].

In the present invention, the measurement and quantitative determination of the target material (reduced glucosylated lysine residual groups) in a test sample can be carried out by subjecting the test sample to an immunoreaction with the above-described reagent. As a solvent to be employed in the measurement system upon conducting the measurement, may be mentioned a usual solvent not affecting deleteriously on the reaction, preferably, a buffer having a pH in a range of about 4–about 8, such as citrate buffer, phosphate buffer, tris-hydrochloric acid buffer or acetate buffer. No particular limitation is imposed on the conditions for the immunoreaction upon conducting the measurement. It is usually possible to employ conditions similar to those used for measurements of the above sort. Namely, the immunoreaction is conducted generally below 45° C., preferably, at about 4°–40° C. for 1–40 hours. The separation of the bound product (B) and the free reactants (F) from each other (B-F separation) after completion of the immunoreaction can be effected by a method known per se in the art. When the solid phase method is employed for example, the solid and liquid phases can be separated from each other by a separation technique such as centrifugation, filtration, washing or decantation. When the other methods are followed, the separation can be conducted by a usual method, for example, the dextran-activated carbon method, double antibody technique or the like.

The measuring method of this invention will hereinafter be described taking the solid phase method, which features a simple operation, by way of example.

(1) First of all, a target substance in a test sample to be measured and a predetermined amount of an insolubilized antigen are competitively reacted with a preset amount of a labelled antibody. Thereafter, B-F separation is effected and the activity of the labelling agent in either one of the B and F is measured to quantitatively determine the amount of the target substance.

(2) First of all, a target substance in a test sample and a predetermined amount of a labelled antigen are competitively reacted with a preset amount of an insolubilized antibody. Thereafter, B-F separation is effected and the activity of the labelling agent in either one of the B and F is measured to quantitatively determine the amount of the target substance.

(3) A target substance in a test sample and an insolubilized antibody are reacted to form an immune complex. A labelled antibody is then reacted with the immune complex and the activity of the labelling agent in the labelled antibody bound to the complex is measured to quantitatively determine the amount of the target substance.

(4) A protein-adsorptive carrier is added to a test sample to adsorb a target substance thereon. A labelled antibody is then reacted with the carrier, followed by measurement of the activity of the labelling agent in the labelled antibody bound on the carrier.

(5) As a test sample, there is used a body fluid which has in advance been subjected to an adsorption treatment with a protein-adsorptive carrier and then to a reducing treatment. A labelled antibody is reacted with the carrier and the activity of the labelling agent in the labelled antibody bound on the carrier is thereafter measured.

In the above manner, the amount of reduced glucosylated lysine residual groups in the test sample can be measured. The thus-measured amount reflects directly the degree of non-enzymatic glucosylation in the subject. Incidentally, the above method (4) or (5) allows to conduct the above-described measuring method in a manner specific to a particular protein in the body fluid. When a carrier bearing "Cibacron Blue" or anti-human albumin antibody immobilized thereon is employed as a protein-adsorptive carrier by way of example, the degree of non-enzymatic glucosylation in a subject can be determined in about two weeks. "CBBG-G250" and "Cibacron Blue" are superior in adsorptive power. Measuring methods making use of carriers with these pigments immobilized thereon are excellent in accuracy.

The degree of non-enzymatic glucosylation, which is measured by any one of the above-mentioned various methods, may be expressed in terms of the number of mole(s) of reduced glucosylated lysine residual groups in a unit protein quantity or in specific, for example, albumin molecules.

By the way, the above-described glucitol-lysine derivative represented by the formula (I) is excellent as a standard substance or labelled antigen, or as a reference material expressed in terms of the number of mole(s) for another standard substance the reacted amount of which is unknown.

A particularly convenient method for practising the measuring method of this invention is to use a kit. Therefore, this invention also provides such a kit. It is important to incorporate the above-described monoclonal antibody as an antibody reagent in the kit. It is possible to add a stabilizing agent such as glycerol or bovine serum protein and/or a preservative to the antibody reagent. Preferably, this antibody reagent takes a lyophilized form. A water-soluble or water-miscible solvent may also be included in the kit. It is also possible to include in the kit a buffer for maintaining a reconstituted reagent system at a constant pH and/or a preservative and/or stabilizing agent for preventing a sample from being spoiled before its use. Although such a buffer is not an essential component for the reagent in the kit, it is preferable to use a buffer which can maintain the pH of the reagent at 4–8 or so upon practising the measuring method of this invention. In addition, the reconstituting agent may preferably contain water. This water may be substituted partly or entirely by a solvent which is miscible with water. Various water-miscible solvents are known to those skilled in the art. Glycerin, alcohols, glycols, glycol ethers and the like may be employed by way of example.

Having generally described the invention, a more complete understanding can be obtained by reference to certain specific examples, which are provided herein for purposes of illustration only and are not intended to be limiting unless otherwise specified.

EXAMPLES

The present invention will hereinafter be described in further detail by the following Examples.

Example 1

Preparation of antigen (1-1) Dissolved in 10 ml of 50 mM PBS (pH 7.4) was 100 mg of β-lipoprotein (product of Sigma Chemical Company), followed by addition of 700 mg of D-glucose and 200 mg of $NaCNBH_3$. The resultant mixture was incubated at room temperature for 4–7 days. Thereafter, acetic acid was added to the reaction system to terminate the reaction and the reaction mixture was dialyzed against distilled water. The thus-dialyzed solution was lyophilized to obtain the intended reduced glucosylated protein (Glc-LDL).

(1-2) Reduced glucosylated proteins and amino acids (Glc-PL, Glc-BSA, Glc-L and Glc-HSA) were obtained respectively in the same manner as in the above procedure (1-1) except that polylysine (furnished by Peptide Institute, Inc.), BSA, lysine and human serum albumin were used separately instead of β-lipoprotein.

(1-3) The glucosylated proteins which had been obtained in the above procedures (1-1) and (1-2) were separately hydrolyzed with 6N-HCl (120° C., 20 hours), followed by amino acid analysis by means of an amino acid analyzer. The ratio of the Glc-L content to the whole lysine content was determined. As a result, it was found to be 29.89% for Glc-LDL, 24.10% for Glc-Pl, 15.56% for Glc-BSA. For Glc-HSA, fractions of about 10% (hereinafter referred to as 10% Glc-HSA) and 61.6% (hereinafter referred to as 61.6% Glc-HSA) were obtained.

(2) Glucitol-lysine derivative (I)

Dissolved in 10 ml of a 1:1 mixed solvent of water and dioxane were 200 mg N-2-(N-benzoylglycyl)-L-lysine (furnished by Peptide Institute, Inc.) and 129 mg of D-glucose, followed by an addition of 100 mg of $NaBCNH_3$. The resultant mixture was incubated at room temperature for 3–4 days. Thereafter, acetic acid was added to the reaction system to terminate the reaction and after distillation, methanol was added, followed by further distillation.

The residue was purified by column chromatography on a "TSK120T Column" (manufactured by Toyo Soda Mfg. Co., Ltd.) [solvent A: 90% acetonitrile, internal standard: 50 mM TFA, solvent B: 5% acetonitrile, gradient: A10% +B90% A60% +B40%]. At a retention time of 9.93 minutes (2 ml/minute), the compound of this invention, namely, N2-(N-benzoylglycyl)-N6-D-Glucitol-L-lysine was obtained. Yield: 58.2%.

A PMR spectrum of the above-obtained compound of this invention is shown in FIG. 1. Principal peaks are as follows:

PMR (DMSO-$d_6$, 2.50 ppm) δ (ppm) (400MH): 8.69 (t,J=6.0), 8.30(m), 8.15 (d,J=7.9), 7.87 (d,J=7.6), 7.54 (t,J=7.6), 7.48 (t,J=7.6), 4.23 (ddd,J=8.3,7.9,4.6), 3.98 (dd,J=16.7,6.0), 3.87 (dd,J=16.7,6.0), 3.67 (dd,J=4.8,1.2), 3.60 (dd,J=10.4,2.8), 3.40–3.51 (m), 3.07 (dd,J=12.5,3.7), 2.94 (dd,J=12.5,8.0), 2.88 (m), 1.74,1.61 (m), 1.34 (m), Further, after hydrolysis (120° C., 20 hours) of the above-obtained compound of this invention in 6N-HCl, an amino acid analysis was conducted by an amino acid analyzer ("HITACHI 835", manufactured by Hitachi Ltd.).

As a result of the analysis, it was confirmed that glycine and glucitol-lysine were substantially in equimolar amounts.

Example 2

Preparation of monoclonal antibody (1) The Glc-LDL which had been obtained in the procedure (1-1) of Example 1 was subcutaneously administered at a dose of 5 μg/mouse to Balb/c mice. The above administration was repeated every second week until 5 times of administration in total so that the mice were immunized. Three days after the final immunization, their spleens were taken out and spleen cells were washed three times with the RPMI-1640 medium.

(2) After washing a mouse myeloma cell strain, P3-U1 [Current Topics in Microbiology and Immunology, 81, 1-7 (1978)] in the same manner as in the above procedure (1), $1 \times 10^6$ cells of the mouse myeloma cells and $1 \times 10^7$ cells of the above spleen cells were placed in a 50 ml centrifugal tube, in which they were mixed together. After centrifugation under $200 \times g$ for 5 minutes, the supernatant was removed by a Pasteur pipette. One milliliter of a 35 W/V % RPMI-1640 solution of "Polyethylene Glycol 2000" (trade name; product of Wako Pure Chemical Industries, Ltd.), which had been maintained at 37° C., was added dropwise, followed by gentle mixing over 10 minutes. Five milliliters of RPMI-1640, which contained 15% FCS and 1 mM pyruvate (hereinafter called "complete RPMI") and had been maintained at 37° C., was added, followed by gentle mixing for 10 minutes. The same amount of the complete RPMI was also added, followed by gentle mixing for 4 minutes. Thereafter, 5 m; of the complete RPMI was added dropwise, followed by gentle mixing for 1 minute. After centrifugation under $200 \times g$ for 5 minutes, the supernatant was removed. After repeating this procedure again, the resultant mixture was suspended in the complete RPMI, which had been maintained at 37° C., to a concentration of $1 \times 10^7$ cells/ml. The suspension was inoculated 1 m; by 1 ml in a 24-well plate (manufactured by Falcon Co.), followed by their culture in a 37° C., 5% carbon dioxide gas incubator. Twenty four hours later, each of the wells was added with 1 ml of the complete RPMI medium containing $1.0 \times 10^{-4}$M hypoxanthine, $4.0 \times 10^{-7}$M aminopterin and $1.6 \times 10^{-5}$M thymidine (hereinafter called "HAT medium"). Thereafter, one half of the supernatant in each well was replaced by a fresh supply of the HAT medium on each of the third, fourth and fifth days. On the sixth day, one half of the supernatant in each well was replaced by the complete RPMI medium containing $1.0 \times 10^{-4}$M hypoxanthin and $1 \times 10^{-5}$M thymidine (hereinafter called "HT medium"). Similarly, one half of the supernatant in each well was replaced by the HT medium on the 6th, 7th and 9th days, and on the 10th day, one half of the supernatant in each well was replaced by the complete RPMI. Thereafter, the cells were allowed to multiply and remain in the complete RPMI medium.

(3) The thus-obtained hybridomas were subjected to cloning by limiting dilution. Namely, the hybridomas and Balb/c mouse thymocytes were mixed in the complete RPMI medium to concentrations of $2.5 \times 10$ hybridomas/ml and $4 \times 10^6$ thymocytes/ml. The thus-prepared mixture was spread at 5 hybridomas/well over a 200-well plate, followed by culture of the hybridomas and thymocytes. The multiplied hybrodimas were subjected at 0.25 hybridoma/well to further cloning in the same manner.

(4) The detection of a clone which produced the intended antibody was conducted by an solid phase method, in which a plate or beads with the above-described antigen (Glc-BSA) was immobilized were used and an anti-mouse goat immunoglobulin (product of Cappel Laboratories Inc.) labelled with $^{125}$I or an enzyme was employed.

Desired hybridomas identified as "Clone No. OAL-M-10" and capable of producing a monoclonal antibody having below-described specific reactivity were obtained accordingly. The thus-obtained hybridoma was deposited in American Type Culture Collection as a deposit number, ATCC HB 9297, on Dec. 19, 1986.

(5) Clone No. OAL-M-10 obtained in the above procedure (4) was cultured at 37° C. for 48 hours in the complete RPMI medium in a 5% carbon dioxide incubator. The culture broth was centrifuged (3000 rpm, 10 minutes), thereby obtaining a culture supernatant which contained the monoclonal antibody of this invention.

The above antibody belonged to the IgG$_2$a subclass. It was confirmed by a test similar to the method proposed by Yeh et al. and employed a rabbit antibody (Litton, Bionetico. Inc. Kensinton, Md. 20795) against various mouse immunoglobulin classes and $^{125}$I labelled protein A [Ming-Yang Yeh et al. Proc. Natl. Acad. Sci., USA, Vol. 76, No. 6, 2927-2931 (1979)].

(6) Suspended in 0.5 ml of the RPMI-1640 medium were $1 \times 10^6$ cells of Clone No. OAL-M-10 obtained in the above procedure (4). The suspension was then administered intraperitoneally to Balb/c mice. Two - three weeks later, the accumulated ascites fluid containing the antibody of this invention was collected in an amount of 2-5 ml per mouse. The concentration of the antibody was about 0.1-1 mg/ml. Five milliliters of the ascites fluid were added with 5 ml of PBS and 10 ml of a saturated ammonium sulfate solution. The resultant mixture was stirred gently at 0° C. A precipitate which had been obtained by centrifugation (10000 rpm × 30 minutes, 4° C.) was subjected to gel filtration through a "Sephadex G-25 Column" (manufactured by Pharmacia AB) which had been equilibrated with 0.05M tris-HCl (pH 8.6). Fractions which were eluted near the void volume were subjected to "Protein A-Sepharose CL-4B" (manufactured by Pharmacia AB) which had been equilibrated with the above-employed buffer, thereby adsorbing the IgG fraction. After washing the column with a 50 mM citrate buffer of pH 5.5, IgG$_2$a was eluted with an acetate buffer of pH 4.3 to obtain a purified antibody, OAL-M-10.

Example 3

Preparation of insolubilized antibody (1) The purified antibody which had been obtained in the procedure (6) of Example 2 was diluted to 20 μg protein/ml with a 50 mM PBS (pH 7.4) containing 0.15M NaCl and 0.05% NaN$_3$.

10,000 polystyrene beads (product of Precision Plastic Co., Ltd., U.S.A.; diameter: 6.4 mm) were thoroughly washed with diluted "Mama Lemon" (trade name; product of Lion Corporation; 1.5 ml undiluted liquid per liter of distilled water), followed by further washing with distilled water. After immersing the polystyrene beads for 3 days in a 0.5M aqueous solution of caustic soda, they were washed until the pH of the washing dropped to about 6.

(2) To 100 ml of the above antibody solution, 800 pieces of the beads were added. The resultant mixture was allowed to stand under reduced pressure for 2 hours with occasional stirring and then at 4° C. overnight. The beads were filtered and washed with saline. Thereafter, the beads were left over under reduced pressure for 2 hours and then at 4° C. overnight, both, in a 50 mM PBS (ph 7.4) which contained 0.5% of crystalline BSA (product of Seikagaku Kogyo Co., Ltd.). The insolubilized antibody was obtained by filtering and thoroughly washing the beads.

Example 4

Preparation of labelled antigen (1) One mCi of Na$^{125}$I (product of NEN Corp.) was added to a solution which had been prepared by dissolving 50 μg of the antigen, Glc-BSA, obtained in the procedure 1-2 of Example 1 in 200 μl of a 0.1M borate buffer (pH 8.2). A dichloromethane solution containing 40 μg of iodogen (product of Pierce Corp.) in 20 μl of dichloromethane was placed in a glass-made testing tube. Under a nitrogen gas stream, the solvent was evaporated to dryness. The above antigen solution was added to the testing tube and was then reacted at 0° C. for 5 minutes with gentle stirring. The reaction product was transferred in a separate testing tube. After terminating the reaction, an albumin fraction corresponding to the peak of radioactivity was collected by gel filtration ("Sephacryl S200", trade name, 1×38 cm; eluent: 50 mM PBS (pH 7.4) containing 0.2% of gelatin], thereby obtaining $^{125}$I-labelled antigen.

Besides, the $^{125}$I-labelled antigen was also obtained in good forms by following the chloramine T method [Nature, 194, 496 (1962)] and the Bolton-Hunter method [Biochem. J., 89, 114 (1963)] respectively.

(2) An enzyme-labelled antigen was prepared by using the lysine residual group of peroxidase. Namely, peroxidase was dissolved to a concentration of 10 mg per ml in a 50 mM phosphate buffer. The solution was then added with 70 mg of glucose and 20 mg of NaBH$_4$. They were reacted at 4° C. for 7 days. After dialysis, purification was conducted by gel filtration and affinity chromatography to obtain the desired labelled antigen.

Example 5

Preparation of labelled antibody

In the same manner as in the procedure (1) of Example 4, $^{125}$I-labelled antibody was obtained by using the purified antibody which had been obtained in Example 2.

Example 6

Preparation of insolubilized antigen

In the same manner as in Example 3, an insolubilized antigen was obtained by using the antigen Glc-PL obtained in the procedure (1-2) of Example 1.

Example 7

Preparation of protein-adsorptive beads (1) After immersing for 4-7 days 5000 polystyrene beads [product of Precision Plastic Co., Ltd., USA; diameter: 6.4 mm] in 700 ml of 80% ethanol containing 1 g of "Coomassie Brilliant Blue (CBB) G-250" (trade name; Serva Feinbiochemica GmbH & Co.), the polystyrene beads were washed with distilled water to prepare the intended protein-adsorptive beads.

(2) One gram of "Cibacron Blue 3GA" (trade name; product of FLUKA AG) in 100 ml of distilled water and 600 pieces of "AMINODYLARK Beads #80" (trade name; diameter: about 6.35 mm; product of Sekisui Chemical Co., Ltd.) were mixed and dispersed with gentle stirring for 5 minutes in a mixed solvent of 300 ml of distilled water and 50 ml of tetrahydrofuran, followed by an addition of 50 ml of a distilled water solution of 10 g of NaCl. After stirring the resultant mixture for 30 minutes, 2.5 m; of an aqueous 5N NaOH solution was added and the thus-obtained mixture was stirred further for 3 days. The reaction solution was removed and the beads were thoroughly washed successively with distilled water, an aqueous 1M NaCl solution, an aqueous 5M urea solution and distilled water in the order mentioned. The beads were thereafter blocked with a 0.01% aqueous gelatin solution to obtain the intended protein-adsorptive beads.

Example 8

Specificity test for antibody (1) Among the antigens obtained in Example 1, the soluble Glc-BSA, Glc-LDL and Glc-L were used as standards. As controls, β-lipoprotein, D-glucose, D-sorbitol, lysine and polylysine were used.

One hundred microliters of a twelvefold solution of the antibody of this invention, which was obtained in the procedure (5) of Example 2, 100 μl of the above standard of the stepwise dilution series or a control, and 100 μl (about 20,000 cpm) of the $^{125}$I-labelled antigen obtained in the procedure (1) of Example 4 were added to 200 μl of an assay buffer (a 50 mM sodium phosphate buffer containing 0.15M of NaCl, 0.1% of gelatin and 0.02% of NaN$_3$, pH 7.4), followed by overnight incubation at 4° C. One hundred microliters of anti-mouse IgG goat antibody (x40; product of Japan Immunoresearch Laboratories Co., Ltd.), 100 μl of normal mouse serum (x 400), and 200 ρl of 12.5% polyethylene glycol, followed by incubation at room temperature for 30 minutes. B-F separation was then conducted, followed by measurement of their radioactivity levels.

Figure 2:
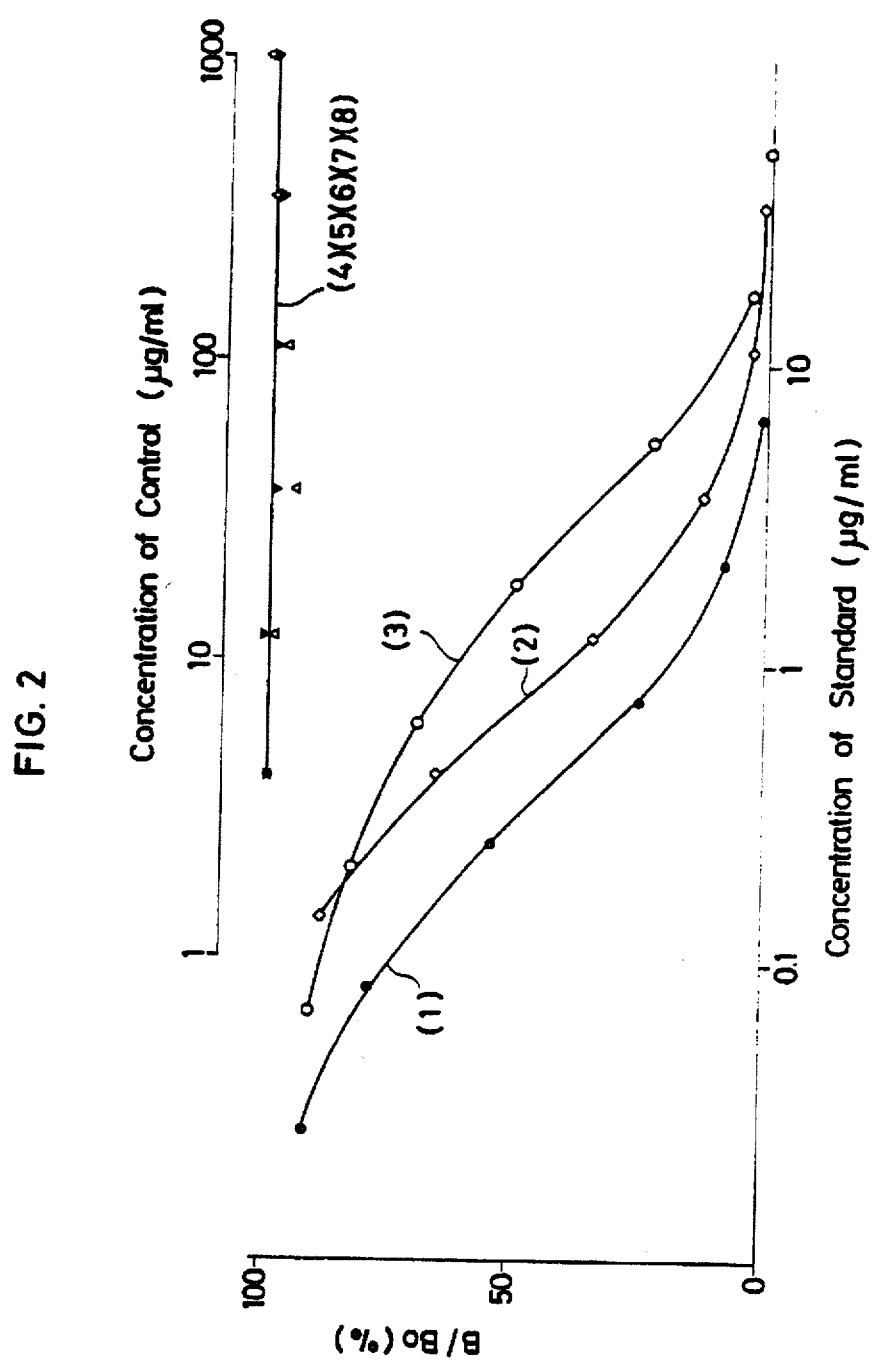
FIG. 2 is a graph showing specificity of the antibody of this invention.

Results are shown in FIG. 2, in which B/B$_0$ (%) are plotted along the axis of ordinates, concentrations of the standard (μg/ml) are plotted along the lower axis of abscissas, and concentrations of control (μg/ml) are plotted along the upper axis of abscissas. In the drawing, (1) indicates results for Glc-BSA, (2) for Glc-LDL, (3) for Glc-L, (4) for β-lipoprotein, (5) for D-glucose, (6) for D-sorbitol, (7) for lysine and (8) for polylysine.

It is apparent from FIG. 2 that the antibody of this invention has extremely high specific reactivity to reduced glucosylated lysine residual groups.

(2) Preparation of standard curve (calibration curve)

Figure 3:
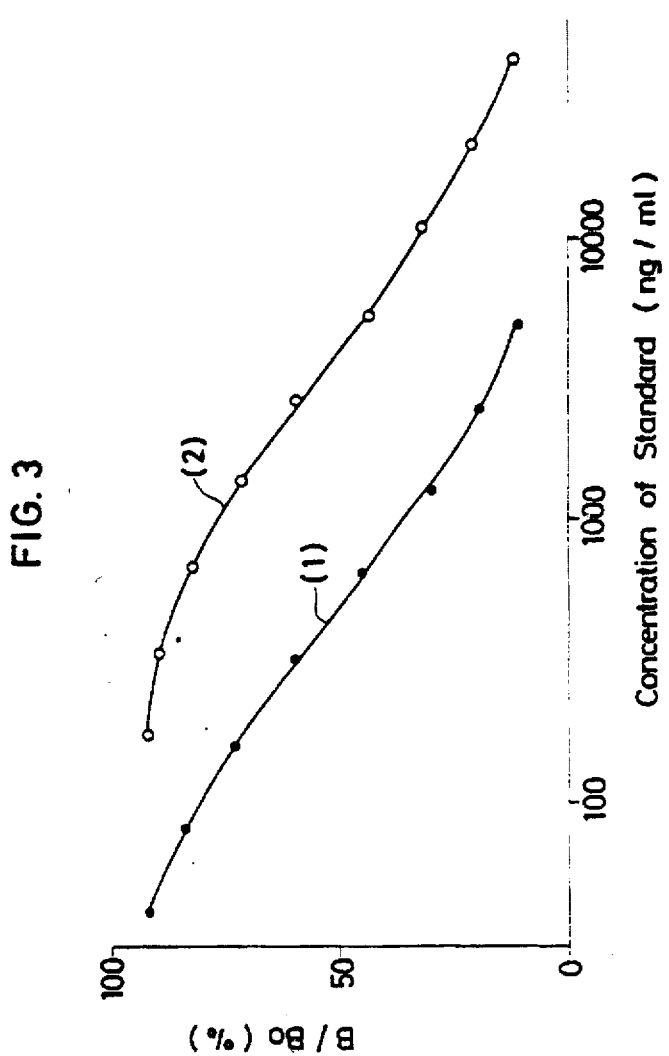
FIG. 3 shows a standard curve (calibration curve) of the measuring method of Example 8.

A standard curve prepared by using the glucitol-lysine derivative (I) as a standard in the above procedure (1) is shown in FIG. 3, in which B/B$_0$ (%) are plotted along the axis of ordinates and concentrations of the standard (μg/ml) are plotted along the axis of abscissas. In the drawing, (1) indicates results obtained by using the glucitol-lysine derivative (I) as a standard while (2) indicates results obtained similarly by using 61.6% Glc-HSA as a standard.

It was confirmed from the drawing that although 61.6% of lysine residual groups were found to be glucosylated in the case of 61.6% Glc-HSA as a result of the above amino acid analysis, Glc-Lys residual groups, which took part in the immunoreaction of 61.6% Glc-HSA, accounted for 28.6% of the whole lysine residual groups by using the glucitol-lysine derivative (I) as a standard.

Example 9

(1) Serum samples were separately collected from a diabetic and a normal subject.

Two milliliters of 80% ethanol were added and mixed with 50 μl of each of the serum samples, followed by centrifugation (3000 rpm × 15 minutes) to obtain a precipitate. The precipitate was dissolved in 500 μl of a 50mM PBS which contained 10 mM NaBH$_4$. The resultant solution was left over for 30 minutes. Thereafter, 10 μl of 5% acetic acid was added to terminate the reaction, followed by an addition of 500 of a 50mM PBS which contained 0.1% of gelatin. The thus-prepared mixtures were used as "test samples".

(2) At 37° C., 100 μl of each of the above test samples and 100 μl (about 40000 cpm) of the $^{125}$I-labelled antibody, which had been obtained in Example 5, were incubated for 1 hour, followed by an addition of one piece of the insolubilized antigen (bead) obtained in Example 6. The resultant mixture was incubated at 37° C. for further one hour. After washing the bead with distilled water, its radioactivity was measured.

As a result, the normal subject and diabetics were clearly distinguished. It was confirmed that the degree of non-enzymatic glucosylation was high in the diabetic group.

(3) One piece of an insolubilized anti-human serum albumin antibody (bead) was added to 250 μl of the above test sample, followed by incubation at 37° C. for 1 hour. After washing the bead with distilled water, about 40000 cpm of the $^{125}$I-labelled antibody obtained in Example 5 was added, followed by incubation at 37° C. for 1 hour. After washing the bead with distilled water, its radioactivity was measured.

Another standard curve was also prepared in the same manner as described above, by using the antigen obtained in Example 1, 10% Glc-HSA, as a standard in place of the above-described test sample. The standard curve is shown in FIG. 4, in which bounded radioactivity (cpm) is plotted along the axis of ordinates while concentrations (ng/ml) of the standard are plotted along the axis of abscissas.

Figure 4:
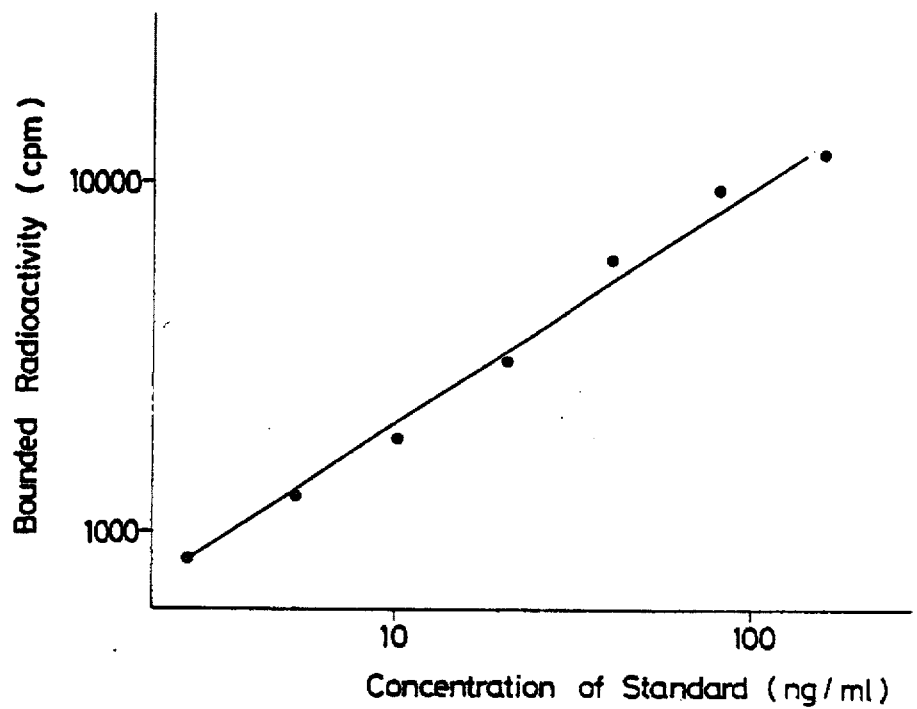
FIG. 4 depicts a standard curve (calibration curve) of the measuring method of Example 9.
Figure 5:
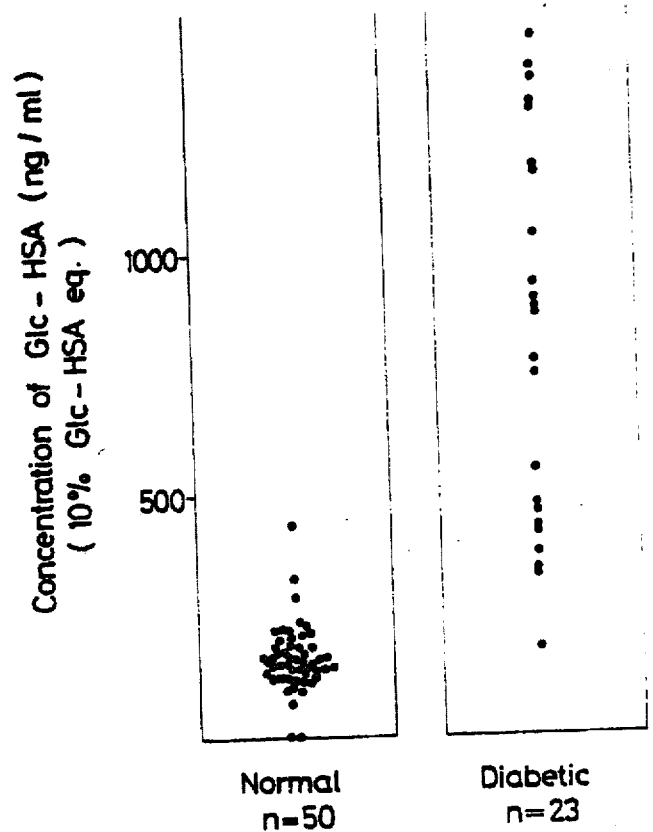
FIG. 5 diagrammatically illustrates measurement results of glucosylated plasma albumin in normal subjects and diabetics, which were measured by the method of this invention.

Measurement results for the above-described test sample are also shown in FIG. 5, in which concentrations of Glc-HSA (ng/ml) (10% Glc-HSA eq.) obtained from the standard curve of FIG. 4 are plotted along the axis of ordinates. These results can be evaluated as the number of mole(s) of glucitol-lysine residual groups by using the glucitol-lysine derivative (I), which was prepared in the procedure (2) of Example 1 as a standard.

Example 10

(1) Glc-HSA was prepared in the same manner as in the procedure (1) of Example 1. It was purified by affinity chromatography on an "Affigel Blue Column" (trade name) to use it as a standard.

As a result of an amino acid analysis, 60.6% of lysine residual groups were glucosylated in the case of the Glc-HSA. By using as a standard the glucositollysine derivative prepared in the procedure (2) of Example 1, the Glc-Lys residual groups which took part in the immunoreaction accounted for 40.5% of the whole lysine residual groups.

The dilution series of the Glc-HSA as a standard [0=blank, 0.39, 0.78, 1.56, 3.1225, 6.25, 12.5, 25.50 picomoles (converted amounts of Glc-HSA residual groups which took part in the immunoreaction) was sampled 20 μl by 20 μl in tubes. Each tube was added with 200 μl of a 10 mM aniline aqueous solution (pH 5) of 30 mM of semicarbazide, followed by gentle shaking. One piece of either protein-adsorptive bead or anti-human serum albumin antibody bead, which was prepared in the procedure (1) or (2) of Example 7, was added to each of the tube, followed by incubation for 30 minutes at room temperature (20°-30° C.).

Thereafter, each reaction mixture was subjected to suction filtration by an aspirator. One to two milliliters of saline were added to wash the bead and the washing was removed completely. This procedure was repeated twice.

On the other hand, 0.3 g of NaBH$_4$ was added to 3 ml of a 0.01N aqueous solution of NaOH to dissolve the former in the latter. 0.5 ml of the solution was added to 25 ml of 0.11M tris-HCl buffer (pH 8.2) which had been chilled well. The resultant mixture was stirred gently to prepare a reducing solution.

Then, 250 μl portions of the reducing solution were separately poured into the respective tubes. The tubes were allowed to stand at room temperature for 30 minutes. Thereafter, the reaction mixtures were each subjected to suction filtration by an aspirator. One to two milliliters of saline were added to each of the tubes to wash the bead and the washing was removed. After repeating this procedure twice, the bead was transferred into another tube.

Subsequent to the above washing of the beads, each tube was added with 200 μl of the $^{125}$I-labelled antibody solution prepared in Example 5.

After conducting incubation at room temperature for 2 hours, the reaction mixtures were each subjected to suction filtration by an aspirator. Each tube was then added with 1-2 ml of saline to wash the bead. The washing was then removed. After repeating this procedure twice, the bead was placed in another tube to measure its radioactivity.

Figure 6:
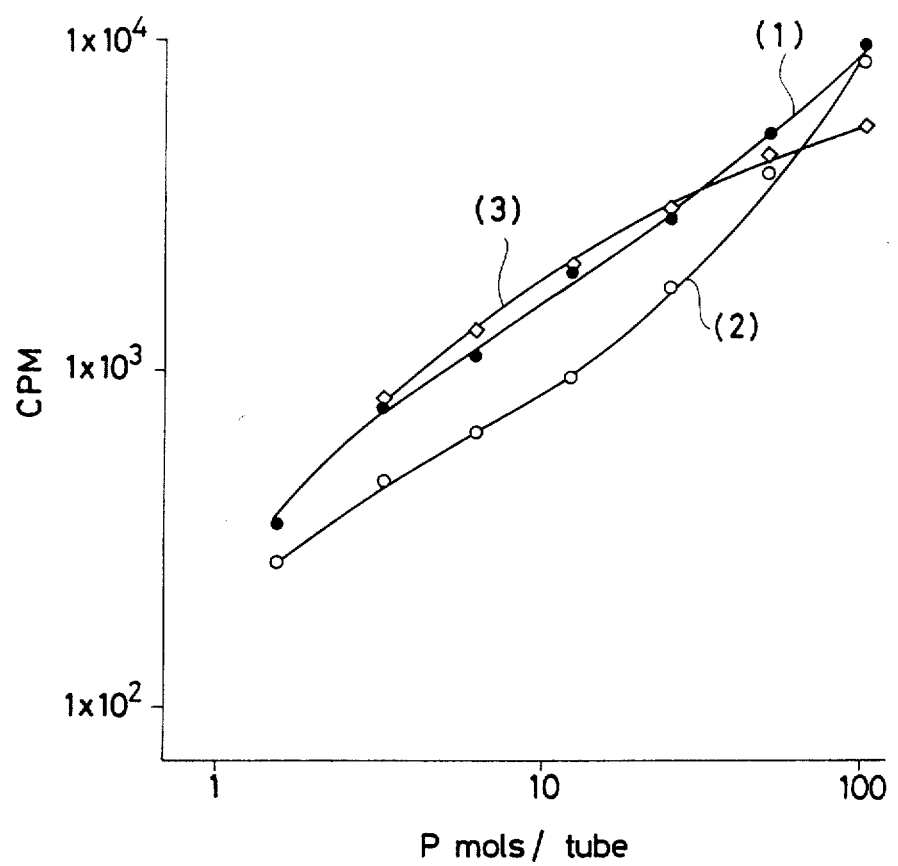
FIG. 6 shows a standard curve (calibration curve) of the measuring method of Example 10.

The thus-obtained standard curve is shown in FIG. 6, in which concentrations of the standard (the number of picomoles of Glc-Lys residual groups, which took part in the immunoreaction, per tube) are plotted along the axis of abscissas while radioactivity (cpm) of the bead (values obtained by subtracting the value of the blank) are plotted along the axis of ordinates. Curves (1)-(3) indicate results obtained by using a carrier with "CBB-G250", a carrier with "Cibacron Blue 3GA", and a carrier with the anti-human serum albumin antibody respectively.

(2) A test was conducted in the same manner as in the above procedure (1) except that 20 μl of the serum of a subject was employed instead of the standard. Results obtained by using a protein-adsorptive carrier with "CBB-G250" are shown in Table 1, in which the amount of reduced glucosylated lysine residual groups is shown in terms of the number of picomoles of immunoreactive Glc-Lys residual groups per bead (the average amount of the adsorbed protein was about 2 μg per bead in the case of HSA) in accordance with FIG. 6.

TABLE 1

| | Number of subjects (n) | Amount of reduced glucosylated lysine residual groups (pmoles/bead) | |
|---|---|---|---|
| | | Average | S.D. |
| Normal subjects | 104 | 0.56 | 0.096 |
| Diabetics | 50 | 4.76 | — |

Having now fully described the invention, it will be apparent to one of ordinary skill in the art that many changes and modifications can be made thereto without departing from the spirit or scope of the invention as set forth herein.

What is claimed as new and is secured by Letters Patent:

1. A method for the measurement of a glucosylated protein in a sample, which comprises subjecting the sample to a reducing treatment and then detecting a protein having one or more reduced glucosylated lysine residual groups with a monoclonal antibody, wherein said monoclonal antibody is one produced by immunization with an antigen selected from the group consisting of reduced glucosylated polylysine, reduced glucosylated human serum albumin, and reduced glucosylated bovine serum albumin.

2. A method as claimed in claim 1, wherein the sample is a protein fraction of a body fluid, said fraction being obtained by an adsorption treatment of the body fluid with a protein-adsorptive carrier.

3. A method as claimed in claim 1, wherein the body fluid is blood.

4. A method as claimed in claim 1, wherein the protein-adsorptive carrier is a Coomassie Brilliant Blue G250- or Cibacron Blue-insolubilized carrier.

5. The method of claim 1, wherein said protein which is detected in said sample is selected from the group consisting of reduced glucosylated human serum albumin and reduced glucosylated bovine serum albumin.

6. A diagnostic kit for diabetes, which comprises a monoclonal antibody produced by immunization of a subject with an antigen selected from the group consisting of reduced glucosylated polylysine, reduced glucosylated human serum albumin, and reduced glucosylated bovine serum albumin.

7. The hybridoma ATCC HB 9297.

8. A monoclonal antibody produced by the hybridoma ATCC HB 9297.

9. A diagnostic kit containing a monoclonal antibody according to claim 8.

* * * * *